United States Patent [19]
Fischer

[11] Patent Number: 6,103,203
[45] Date of Patent: Aug. 15, 2000

[54] SYSTEM AND METHOD FOR CONTROLLING A LIGHT ACTUATOR TO ACHIEVE PARTIAL POLYMERIZATION

[75] Inventor: Dan E. Fischer, Sandy, Utah

[73] Assignee: Ultradent Products, Inc., South Jordan, Utah

[21] Appl. No.: 08/912,031

[22] Filed: Aug. 15, 1997

[51] Int. Cl.⁷ ............................. B01J 19/08; A61C 13/15
[52] U.S. Cl. ........................... 422/186; 433/29; 433/226; 433/228.1; 422/129; 422/131
[58] Field of Search .................. 433/29, 226, 228.1; 422/186, 129, 131

[56] References Cited

U.S. PATENT DOCUMENTS

| 4,450,139 | 5/1984 | Bussiere et al. | 422/186.3 |
| 4,501,558 | 2/1985 | Maliga | 433/86 |
| 5,554,855 | 9/1996 | Ueno | 250/455.11 |
| 5,634,711 | 6/1997 | Kennedy et al. | 362/119 |

*Primary Examiner*—Hien Tran
*Assistant Examiner*—Frederick Varcoe
*Attorney, Agent, or Firm*—Workman, Nudegger & Seeley

[57] ABSTRACT

A system and method for achieving partial polymerization of a photoreactive resin include: (i) light source means for providing light energy to the photoreactive resin, the light source means having an intensity; (ii) timing means for causing the light source means to provide light energy to the photoreactive resin for an illumination time, during which the light source means provides light energy to the photoreactive resin, the timing means selectively operable in a plurality of different time increments, thereby allowing fine tuning of the total amount of light energy provided to the photoreactive resin; and (iii) power supply means electrically coupled to the light source means and the timing means for supplying electrical power to the light source means and the timing means. In one embodiment, the system is programmed to automatically achieve a constant total light energy output despite variations in the intensity of the light source means. The system may also pulsate and is operable in a full cure and partial cure mode.

32 Claims, 4 Drawing Sheets

SYSTEM AND METHOD FOR CONTROLLING A LIGHT ACTUATOR TO ACHIEVE PARTIAL POLYMERIZATION

BACKGROUND OF THE INVENTION

1. The Field of the Invention

This invention is in the field of light curing units employed in the polymerization of photoreactive resins.

2. The Relevant Technology

Light activation units, also known as light curing units, are employed to polymerize photoreactive resins in a variety of industries. Light activation units typically include a light source having a certain intensity and a timer which controls the illumination time during which the light source emits light energy.

Typically, before actuating the light curing unit, the practitioner measures the intensity of the light source, then manually sets the timer for a desired illumination time. Upon actuating the unit, the timer causes the unit to emit light for the selected illumination The total light energy emitted per area of resin is the product of the intensity of the bulb multiplied by the illumination time. In other words, the total light energy emitted is the product of the wattage of the bulb multiplied by the illumination time.

In the field of dentistry, for instance, light curing units are often employed to polymerize photoreactive resins, such as light curable resins, composites, and other polymers containing photoinitiators. By way of example, a photoreactive resin is often employed to attach a dental appliance such as a veneer to a dental surface. The resin is disposed on the veneer, after which the veneer is placed against the tooth. The light curing unit is then directed toward the translucent veneer and actuated for a selected illumination time, emitting a total light energy into the resin. The light energy polymerizes the resin, maintaining the veneer firmly in place.

Typical light curing units are designed to emit a total light energy such that the photoreactive resin is polymerized, transforming the photoreactive resin from a liquid state to a solid state. These units are typically designed so that light curing units emit light in increments of tens of seconds. Thus, the practitioner only has the option of setting the time to produce an illumination time of ten seconds, twenty seconds, thirty seconds, and so on up to sixty seconds. As a result, the practitioner does not have the option of fine tuning the illumination time to transform the photoreactive resin from the liquid state to a desired state intermediate to the liquid state and the solid state.

One difficulty with these typical light curing units is that once a photoreactive resin is in the solid state, it is difficult to remove excess resin disposed on a dental surface without damaging the underlying dental surface or the dental appliance attached by the resin. In addition to causing unsightly physical appearance, excess resin disposed on a dental surface can cause a deformed tooth structure, interfering with the smooth functioning of a particular dental surface and/or cause soft tissue problems.

When excess resin is applied to bond the dental appliance to the tooth, which often occurs during dental restorations, the practitioner may be required to damage the dental appliance or damage the underlying dental surface in order to remove the excess. Even if the dental appliance or dental surface is not damaged during removal of the excess, the practitioner may be required to grind off hardened resin. The grinding, breaking, or scraping of hard material required to clean off the excess resin is labor intensive.

Furthermore, even in the liquid state, photoreactive resins are difficult to remove from a dental surface. If a liquid resin is placed on a surface, it often leaves a resin film despite various attempts to wipe off the liquid resin.

Another difficulty with typical light curing units is that light curing units are also employed to polymerize photoreactive flowable type resins disposed on or within a tooth as filling material. Because of the liquid nature of these resins, the resins often migrate from the desired surface, flowing out of a hole drilled in a tooth, for example. In an attempt to prevent undesired migration, practitioners have constructed a mold surrounding the tooth designed to retain liquid resin in a desired area.

Although it is possible for a practitioner to actuate a typical light curing unit and manually turn the unit off when a desired illumination time has been reached, thereby achieving a resin stage intermediate the liquid and solid stages, the practitioner is required to simultaneously view a clock or otherwise keep track of the time or the nature of the resin during the procedure, which is inconvenient while working inside a patient's mouth, for example. Furthermore, it is difficult, if not impossible to accurately, consistently, reproduce such a manual procedure. In addition, the desired illumination time may be in the tenths or hundredths of seconds, compounding the difficultly of accurately, consistently reproducing the total energy provided to a particular polymer when using a manual procedure.

Another difficulty within the art is that the light source of a typical light curing unit often experiences variations in light intensity. These variations are typically decreases in intensity caused by decreases in voltage, amperage, or by deteriorating bulb condition. For example, tungsten from the filament of a light bulb can be deposited on the inside of the bulb, decreasing the intensity of the bulb. Over time, decreases in intensity become more noticeable.

Variations in intensity make it even more difficult for the practitioner to provide a total light energy to a photoreactive resin which will cause the resin to achieve an intermediate stage. Typically, the practitioner must compensate for these variations by manually increasing the illumination time or by replacing a light bulb. However, it is uneconomical to replace a light bulb whenever a decrease in intensity occurs. Furthermore, monitoring the intensity of the bulb and manually adjusting for intensity variations is cumbersome.

Another problem within the art relates to the continuous nature of typical light curing units. Typical light curing units provide illumination without interruption. It is believed that when photoreactive resins are cured on a continuous basis, the photoreactive resins suffer from polymeric shrinkage, stress and strain. Shrinkage, stress, and strain result in a weaker bond and/or seal or potentially converts to stress on teeth.

SUMMARY AND OBJECTS OF THE INVENTION

It is therefore an object of the invention to provide an improved light-curing unit.

It is another object of the invention to provide a light-curing unit capable of selectively, partially polymerizing or "tacking" a photoreactive resin.

It is another object of the invention to provide a light-curing unit which is selectively operable in a partial-cure mode as well as a full-cure mode.

It is another object of the invention to provide a fine-tuned light curing unit which is actuated for variable increments of time, the increments controllable by the practitioner.

It is another object of the invention to provide a fine-tuned light curing unit which is actuated for small increments of time.

It is another object of the invention to provide an internally adjusting light-curing unit which is capable of being programmed to emit a constant, reproducible desired total light energy for selected procedures despite variations in the intensity of a light source used to illuminate a resin.

It is another object of the invention to provide compensating means for compensating for variations in the intensity of the light source means, thereby providing a constant, reproducible total light energy output.

It is another object of the invention to provide a device which is retrofit onto existing light-curing units that provides for variable increment capability and compensating capability.

It is another object of the invention to provide a pulsating light curing system.

It is another object of the invention to provide a constant, reproducible quantity of light energy without manually adjusting the illumination time and without continually replacing a light bulb.

The light curing unit of the present invention is selectively operable in a full-cure mode, a partial-cure mode, an automatic time selecting mode, and a manual time selecting mode. In the partial-cure mode, the light curing unit emits a total light energy which will partially polymerize the photoreactive resin only until the resin reaches a desired amount of polymerization. In the full cure mode, the resin is fully polymerized until it reaches a permanent, solid state. The unit is optionally retrofit onto an existing light curing unit.

Partially polymerizing (also known as partially curing) the photoreactive resin is a process referred to herein as "tacking" the photoreactive resin. By initially tacking the photoreactive resin to a dough, gel, slush, or slightly rubbery state for example, the practitioner is able to prevent undesired migration of resin and clean off excess resin before curing the resin permanently in place. Turning again to the example of the veneer, rather than immediately fully curing the adhesive between the veneer and the dental surface, the practitioner sets the light curing unit to the "tack" mode, tacks the adhesive, then removes the excess portion of resin. The partially polymerized nature of the tacked resin allows all or substantially all of the resin to be wiped off as a manageable "slush" or pulled off in one cohesive, doughy, mass or multiple cohesive pieces, rather than leaving an annoying film which often occurs with liquid stage cleanup attempts and rather than breaking, scraping, or grinding off solid, hardened material.

To rely on tacking as a fine tuning method to aid in cleanup, it is particularly important that the total light energy output is reproducible. Otherwise, too much energy may be applied, over-solidifying the resin, making cleanup more difficult or compromising the set resin strength and/or jeopardizing the integrity of the material's desired contours. Thus, once it is determined how much energy is required to tack a particular photoreactive resin to the desired stage, the light-curing unit may be programmed to reproduce the same total light energy each time.

The light curing unit comprises compensating means for compensating for variations in the intensity of the light source means such that the total light energy provided to the resin is constant despite these variations. The compensating means may be programmed with the desired total light energy and adjusts the system to emit the desired total light energy upon receiving a measurement of the intensity of the light source. The light curing unit thus compensates for variations in light intensity, thereby emitting a preprogrammed constant desired total light energy in the partial and/or full cure modes. The compensating means may be configured to compensate for variations in intensity in the manual and/or automatic time selecting modes.

The automatic time selecting mode is one example of the compensating means. In one embodiment of the automatic time selecting mode, upon metering the light source, the light curing unit automatically selects an illumination time required to emit the desired, preprogrammed total light energy. As a result, it is possible to reproducibly provide the same amount of light energy for each actuation, despite variations in the intensity of the light source means. In the manual selecting mode, the practitioner manually adjusts the illumination time to provide the desired total light energy.

In the automatic time selecting mode, as the intensity of the light source means decreases, the light-curing unit can automatically compensate by increasing the illumination time. In another embodiment, in either of the manual and/or automatic time selecting modes, the light curing unit compensates for variations in light intensity by increasing the voltage, current or by adjusting other features. As a result, the practitioner is able to provide a constant, reproducible desired total light energy for a given procedure without manually adjusting the timer and/or without replacing a light bulb each time bulb output changes.

The total light energy required to tack the photoreactive resin until it reaches the partially-polymerized state should be calculated precisely because it is important to provide only that energy which will tack the photoreactive resin to the desired state. The partially-polymerized state is often surpassed as light is emitted from the light curing unit. Unless care is taken to reach the desired amount of curing, the light curing unit will fully polymerize the resin to a solid state. In order to achieve the desired stage, which often occurs in illumination times of less than ten seconds, the light curing unit may be fine tuned to deliver a precise amount of light energy.

To achieve this fine tuning, the light curing unit of the present invention is selectively operable in a plurality of different time increments such as increments in the thousandths of seconds, hundredths of seconds, tenths of seconds, seconds, tens of seconds, minutes, or combinations thereof.

The statement that the timing means is "selectively operable in a plurality of different time increments," or similar phrase as used throughout this specification and the appended claims, means that at least two different time increments may be selected, rather than merely a single increment in the tens of seconds, for example. The available increments include, for example, increments in the thousandths of seconds, hundredths of seconds, tenths of seconds, seconds, tens of seconds, minutes, or combinations thereof. Thus, the light curing unit may be set for an illumination time featuring minutes, tens of seconds, seconds, tenths of seconds, hundredths of seconds, or combinations thereof, such as (i) thirty three and two tenths seconds; (ii) one minute; (iii) seven tenths of a second; (iv) forty seconds; or (v) twenty three and fourteen hundredths seconds. By having a sensitivity into the tenths, hundredths, and even thousandths of seconds, the light curing unit may employ the precisely desired light energy.

As another aspect of the invention, it is possible to employ an overriding means for manually overriding the illumination time automatically selected by the light-curing unit. As another feature of the invention, a variety of features of the present invention are retro-fit onto existing light-curing units to provide tacking capability and reproducible total light energy capability.

The light-curing unit is comprised of a light source means for providing light energy to the photoreactive resin, the light source means having an intensity. The light curing unit further comprises timing means for causing the light source means to provide light energy to the photoreactive resin for an illumination time, during which the light source means provides light energy to the photoreactive resin. The timing means is a timer is selectively operable in a plurality of different time increments, thereby allowing fine tuning of the total amount of light energy provided to the photoreactive resin. The timing means thereby controls the total amount of light energy provided to the photoreactive resin.

The timing means includes time selecting means for selecting the illumination time. A power supply means is electrically coupled to the light source means and the timing means for supplying electrical power to the light source means and timing means. The light curing unit also includes metering means for measuring the light output of the light source means.

The time selecting means is capable of selecting an illumination time having a plurality of different time increments. This variable increment capability of the timing means allows the practitioner to tack the resin for a precise amount of time.

In one embodiment, the compensating means comprises the time selecting means comprising automatic time selecting means electrically coupled to the metering means for automatically selecting an illumination time. Between and/or during actuations, the automatic time selecting means compensates for light output loss by increasing the selected illumination time. In another embodiment, the compensating means is separate from the time selecting means.

By way of example, while a light curing unit programmed with a measurement of the desired total light energy is in the automatic time selecting, tacking mode, the practitioner directs the light source means into the metering means, which may be integral within the light curing unit. The metering means receives the light emission, measures the intensity of the light source means, and communicates the intensity measurement to the automatic time selecting means. The automatic time selecting means receives the measurement of the intensity and determines an illumination time which will achieve the desired total light energy output required for the desired stage of tacking then communicates a measurement of the illumination time to means for causing the light source means to provide light energy to the photoreactive resin for the selected illumination time. The practitioner directs the light source means toward the photoreactive resin and actuates the light curing unit. The timing means allows the light curing unit to emit energy only for the selected illumination time, tacking the resin, but not solidifying the resin. After the practitioner has tacked the resin, optionally, the practitioner wipes away excess resin, adds additional resin or performs a variety of other procedures. The practitioner can then tack the additional resin, for example.

The compensating means compensates for variations in light intensity either during the actuation or between actuations. For example, in one embodiment, after the initial actuation, the practitioner meters the intensity of the light source means again. In the event of a decrease in light intensity, the compensating means may increase illumination time or electrical power provided to the light source means or otherwise adjust to compensate for the loss of intensity. Once the practitioner has tacked the resin, the practitioner can adjust the light curing unit to the full cure mode, then polymerize the resin until it achieves the fully polymerized, solid state.

While examples such as mounting a veneer have been used to illustrate the advantages of the preferred light curing unit, it will be appreciated that the tacking of photoreactive resins is advantageous in a variety of settings, including (i) preventing undesired migration of resin during a variety of direct restorations, such as when employing a flowable resin applied with a syringe; (ii) cleaning off excess resin during a variety of indirect restorations, such as implanting an in-lay into a tooth; or (iii) building up a particular dental surface. When inserting a flowable resin within a hole prepared in a tooth, for example, it is possible to prevent undesired migration by tacking the resin. Adjustments may then be made without migration of the resin. For example, after the resin has been tacked, additional resin may be added, thereby building up a particular dental surface. The additional resin may be added without the initial resin flowing in an undesired direction. Once the resin is in a desired position, and excess resin has been removed, the resin may be fully cured.

As another feature of the invention, it is possible to pulsate the illumination provided by the light curing unit. In addition, because of the variable increment capability of the invention, it is possible to pulsate in a variety of different time increments. By pulsating, the light curing unit provides light energy on a non-continuous basis, more gradually polymerizing the resin, which results in a stronger polymeric bond and prevents polymeric shrinkage, stress and strain on the resin. Thus, the light curing unit also includes a pulsating mode.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The headings used in this specification are for convenience in describing the invention only and should not be considered as limiting in any sense.

Figure 1:
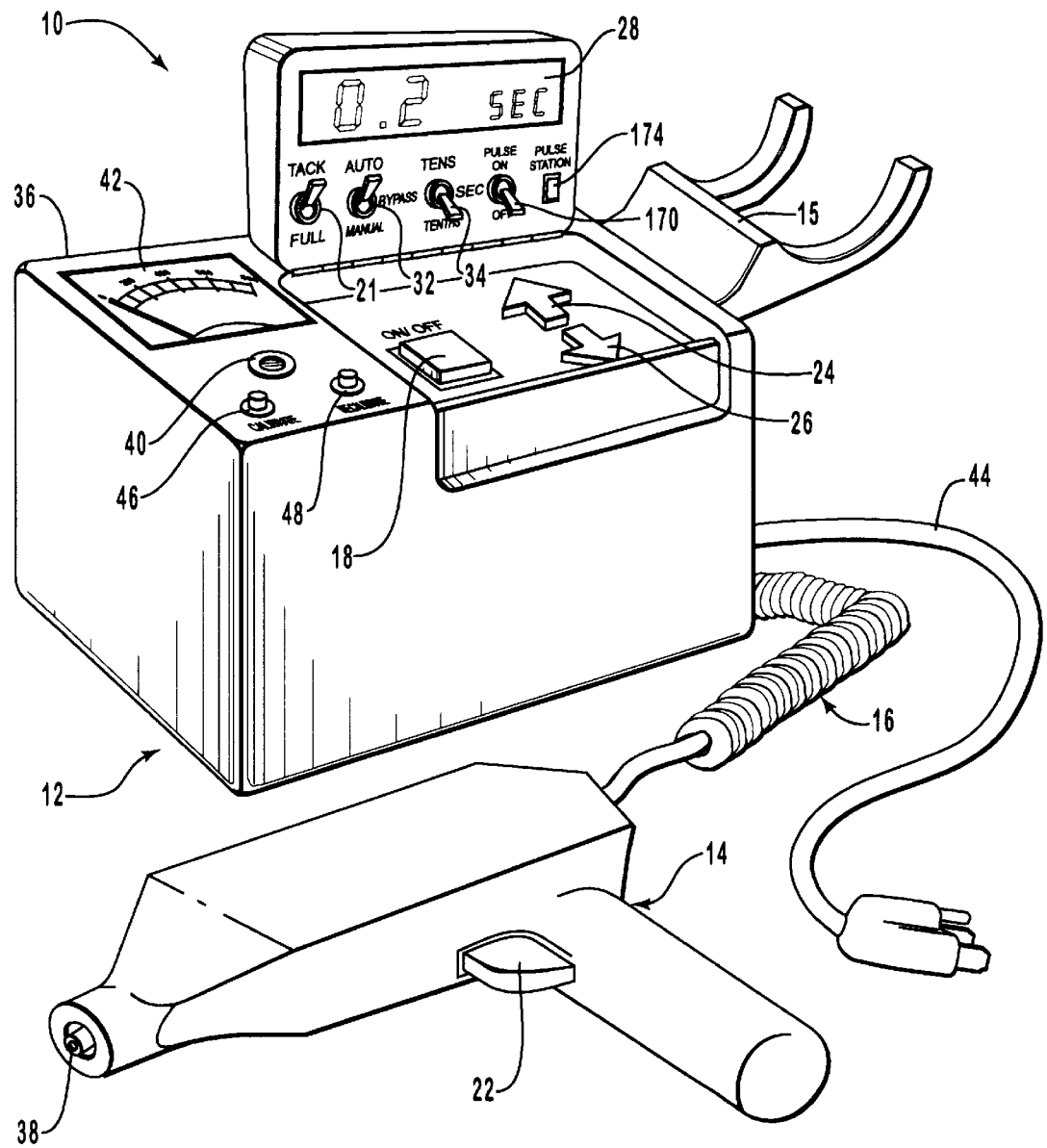
FIG. 1 is a perspective view of one embodiment of the light curing unit of the present invention.

The light curing system 10 of the present invention, shown in FIG. 1, is designed to provide light energy to photoreactive resin in a partial-cure mode (also known as a "tack" mode) and, optionally, in a full-cure mode. In the partial-cure mode, the light curing system partially polymerizes the resin such that the resin achieves a slurry state, a slushy state, a doughy state, a gel state, a slightly rubbery state, or a variety of other states in transition between a liquid state and a solid state. Each of the foregoing partially polymerized states are referred to collectively herein as a "tacked" state. Each of the various tacked states may have its own advantages. For example, it may be more convenient to wipe excess resin off when the resin is in the form of a slush than when the resin is in the form of a dough or slightly rubbery. Cleaning the resin when in a slush stage is less likely to disturb the integrity of the resin.

In the fully polymerized state, the resin is solid and intended to be permanent to hold a veneer or in-lay in place or fill a tooth, for example. After the photoreactive resin achieves the desired partially polymerized state and any necessary adjustments have been made, such as removal of excess resin, or addition of more resin, the light curing system 10 may be adjusted to the full cure mode and actuated, curing the photoreactive resin until the resin achieves the solid, or fully polymerized state.

Light energy is provided by light source means for providing light energy to the photoreactive resin. The light curing system 10 further comprises timing means for causing the light source means to provide light energy to the photoreactive resin for an illumination time. The timing means thus controls the total amount of light energy provided to the photoreactive resin. The timing means is selectively operable in a plurality of different time increments, thereby allowing fine tuning of the total amount of light energy provided to the photoreactive resin. Thus, the photoreactive resin achieves and at least temporarily remains in a partially-polymerized state. In light of this fine tuning ability, the practitioner is able to initially tack the photoreactive resin to a desired stage with confidence that the resin will not be overpolymerized.

The timing means includes time selecting means for selecting an illumination time. Various embodiments of time selecting means will be discussed, including a manual and an automatic time selecting means. The time selecting means selects an illumination time which may have a number of different time increments. The invention further includes metering means for measuring the intensity of the light source means.

In one embodiment, the time selecting means comprises automatic time selecting means electrically coupled to the metering means for automatically selecting the illumination time. The automatic time selecting means may be programmed with a measurement of the total light energy desired to tack and/or fully polymerize the resin. The automatic time selecting means may also be programmed such that upon receiving a measurement of the light intensity, the automatic time selecting means selects an illumination time which is required to achieve the desired total light energy.

As an example, in one embodiment, when employing such a programmed light curing system 10, the practitioner positions the light source means adjacent the metering means. The practitioner then actuates the light source means and the metering means measures the intensity. The measurement of the light intensity is directed to the automatic time selecting means. The automatic time selecting means then selects an illumination time which will achieve the desired total light energy output based on the metered light intensity. The illumination time is communicated to means for causing the light source means to provide light energy to the photoreactive resin for the selected illumination time, which permits illumination only for the selected time.

After a series of actuations (or during a single actuation) the intensity of the light source means typically decreases. By metering the intensity of the light source means after the initial actuation, if the intensity has decreased, the automatic time selecting means selects a longer illumination time, which is communicated to the means for causing the light source means to provide light energy to the photoreactive resin for the selected illumination time, thereby compensating for the variation in light intensity. Therefore, the light curing system 10 provides constant, reproducible desired total light energy for achieving the partially polymerized state, and optionally, the fully polymerized state despite variations in the intensity of the light source means.

Thus, system 10 comprises compensating means for compensating for variations in light intensity. In one embodiment, the automatic time selecting means itself acts as a compensating means. In another embodiment, the compensating means is separate from the time selecting means. Other examples of the compensating means will be discussed below.

With continued reference to FIG. 1, the light curing system 10 of the present invention is comprised of a main housing 12 and a light source housing 14 coupled to the main housing 12 by an electrical cord 16. Cradle 15 cradles light source housing 14 for convenient storage. Light source housing 14 is configured to be disposed within a patient's mouth or to be used in other areas where illumination of photoreactive resin is desired. An "on/off" button 18 is provided to selectively turn system 10 on and off. A means for selecting between a full-cure mode and a partial cure mode, such as knob 21 is also provided. Knob 21 is electrically coupled to the time selecting means.

I. Light Source Means

Light source housing 14 houses the light source means for providing light energy to the photoreactive resin, the light source means having a certain intensity. Examples of the light source means include any kind of light source, including, for example, various bulbs, such as halogen bulbs. The halogen bulb may have an intensity in the range of approximately 100 to 125 Watts, for example. Other examples of light source means include incandescent bulbs, fluorescent bulbs, laser sources, and light emitting diodes. In one embodiment, the light source means emits white light through a blue filter, creating a blue light, as is understood by those skilled in the art. Trigger 22 actuates the timing means, which is preferably disposed within main housing 12. The actuation of the timing means actuates the light source means, as will be discussed in more detail below.

In a preferred embodiment, light source housing 14 further houses a fan (not shown) for cooling the light source means. The fan is actuated upon actuation of the light source means and is turned off by a thermal control switch. Also in a preferred embodiment, a probe means such as a fiber optic wand (not shown) having a fiber optic bundle is coupled to the light source means for focusing the light source means. Also in a preferred embodiment, a translucent shield (orange for example) may be disposed on light source housing 14 to protect the practitioner's eyes during actuation of the light source means.

Photoreactive resins include a variety of monomers and polymers having photoinitiators employed in dental applications and other fields, which polymerize upon contact with light. Examples of such photoreactive resins include light curable resins, composites, luting agents, cements, and fissure sealants. The term "photoreactive resins" encompasses both filled and unfilled resins.

II. Metering Means

The integral meter 36 shown in FIG. 1 is an example of a metering means for measuring the intensity of the light source means. Other examples of metering means include separate meters, or other light meters commonly known in the art. In one embodiment, the metering means is electrically coupled to the compensating means or a time selecting means separate from the compensating means or to a variety of other components of system 10. Feedback circuitry, for example, may be provided between the metering means and the time selecting means or other components. In operation, the practitioner positions distal end 38 of light source housing 14 adjacent sensor 40 of meter 36 and presses trigger 22 to meter the intensity of the light source means.

The meter display 42 demonstrates the intensity of the light source means so that the practitioner may manually select the illumination time, if desired. In one embodiment, the metering means communicates a measurement of the intensity to the automatic time selecting means, which determines the illumination time based on the measurement and on the measurement of the desired total light energy.

Sensor 40 may be located in a variety of positions within system 10. As shown in FIG. 1, in one embodiment, sensor 40 is located on housing 12. In yet another embodiment, a sensor of the metering means is disposed within light source housing 14, thereby allowing the practitioner to meter the intensity of the light source means, without positioning the light source means adjacent a sensor 40 and housing 12. In one embodiment, the intensity is metered when trigger 22 is actuated and the timing means is actuated after the illumination time has been selected by the time selecting means.

The metering means may include means for communicating a measurement of the intensity of the light source means to the compensating means, such as means for communicating a measurement of the intensity to the automatic time selecting means. An example of the means for communicating the intensity measurement is circuitry electrically coupling the metering means and the compensating means.

III. Timing Means

As discussed above, the invention further includes timing means for causing the light source means to provide light energy to the photoreactive resin for an illumination time. The timing means controls how long the light source means illuminates the photoreactive resin once trigger 22 has been actuated. The timing means thus controls the total amount of light energy provided to the photoreactive resin.

The timing means is preferably selectively operable in a plurality of different time increments, for fine tuning of the total amount of light energy provided to the photoreactive resin. In light of the variety of time increments available, the practitioner is able to fine tune the percentage of polymerization and achieve programmed, fine control of the light output. Examples of optional time increments which a practitioner or the automatic time selecting means can select include increments in the: (a) tens of seconds, e.g. 10, 20, 30; (b) seconds, e.g. 1, 2, 3; (c) tenths of a second, e.g. 0.1, 0.2, 0.3, (d) hundredths of seconds, e.g. 0.01, 0.02, 0.03., or combinations thereof. Other time increments, such as minutes and thousandths of seconds, or combinations of the same are also possible.

As discussed previously, currently available technology typically does not provide for fine tuning of the illumination time, but instead provides for time increments in the tens of seconds, such as ten, twenty, thirty, forty, fifty, and sixty second illumination times. By providing the ability to emit light in a controlled fashion for reproducible, fine tuned time increments, the practitioner is able to fine tune the amount of light energy provided to the photoreactive resin.

In one embodiment, upon actuation of trigger 22, the timing means begins an illumination time sequence and the light source means begins emitting light for the illumination time. Upon the expiration of the illumination time, the timing means turns off the light source means.

In one embodiment, the timing means is electrically coupled to the power supply of the light source means and activates the power supply at the beginning of the illumination time sequence, then terminates the power supply of the light source means at the end of the illumination time sequence. In one embodiment, light is emitted only while trigger 22 is in the actuated mode. Thus, for safety purposes, if the practitioner releases trigger 22, the light source means stops emitting light regardless of the illumination time programmed in the timing means.

The timing means includes (i) time selecting means for selecting an illumination time during which the light source means provides light energy to the photoreactive resin, and (ii) means electrically coupled to the time selecting means for causing the light source means to provide light energy to the photoreactive resin for the selected illumination time.

In one embodiment, the time selecting means comprises means for manually selecting the illumination time. The means for manually selecting the illumination time may be used to select the illumination time for the full cure mode or the partial cure mode, or both. In one embodiment, the manual time selecting means includes illumination time increase knob 24 and illumination time decrease knob 26, which are electrically coupled to the means for causing the light source means to provide light energy to the photoreactive resin for the selected illumination time and allow the practitioner to manually adjust the illumination time after viewing a measurement of the intensity of the light source means in display 42 or in a separate display. A chart may be mounted on the system 10 or in another convenient location, indicating recommended illumination times for certain intensities.

A display means for displaying the selected illumination time, such as display 28, is electrically coupled to the timing means for displaying the illumination time selected either manually or automatically by the time selecting means.

As discussed, in one embodiment, the time selecting means comprises an automatic time selecting means for automatically selecting an illumination time. The automatic time selecting means is electrically coupled to the metering means and the means for causing the light source means to provide light energy to the photoreactive resin for the selected illumination time. The automatic time selecting means selects the illumination time based on a measurement of the desired total light energy and on a measurement of the intensity of the light source means. In yet another embodiment, the time selecting means comprises both a manual time selecting means and an automatic time selecting means such that either mode is available.

In one embodiment, the automatic time selecting means is programmed with the equation that the illumination time is the quotient of the desired total light energy divided by the wattage of the light source means or a similar equation. The intensity it typically measured in terms of Watts/$M^2$ or a derivative thereof such as milliwatts/$cm^2$. Thus, one example of such a similar equation is that the illumination time is the quotient of the desired total light energy divided by the intensity and by the area illuminated. Upon determining the desired total light energy for tacking and full cures for a particular resin, the practitioner is able to input a measurement of the desired total light energies for each mode by further programming the automatic time selecting means. As one method of programming the automatic time selecting means, the compensating means includes a calibrating means for calibrating system 10 with a measurement of the desired total light energy, as will be discussed below.

Upon being so programmed and upon receiving a measurement of the intensity from the metering means, the automatic time selecting means selects the illumination time which is required to emit the desired total light energy for the selected mode in light of the measured intensity. The automatic time selecting means then communicates a measurement of the illumination time to the means for causing the light source means to provide light energy to the photoreactive resin for the selected illumination time. This process can be repeated multiple times by metering the light source means following successive actuations. As intensity decreases, illumination time increases to compensate for the decrease. The automatic time selecting means is thus programmed such that system 10 reproducibly provides the desired total light energy for achieving the partially polymerized state, and optionally, the fully polymerized state, despite variations in the light intensity.

As an example, after a first actuation, the practitioner can again measure the intensity of the light source means by placing the light source means adjacent the metering means and actuating system 10. Upon receiving the measurement of the light intensity, if the intensity has decreased, the automatic time selecting means selects an illumination time which is greater than the previous illumination time and communicates a measurement of the updated illumination time to the means for causing the light source means to provide light energy to the photoreactive resin for the selected illumination time, which allows illumination during the next actuation based on the updated illumination time.

In one embodiment, light curing system 10 includes overriding means for manually overriding the illumination time selected by the automatic time selecting means. As discussed above, the selected time is displayed on monitor 28. If the overriding means is in operation, the practitioner may view the monitor and decide whether or not to illuminate the photoreactive resin for the selected illumination time. In the event the practitioner desires to manually adjust the illumination time, the practitioner may employ knobs 24, 26, to adjust the illumination time, thereby overriding the selected illumination time. In the automatic time selecting mode with override capability, also known as the bypass mode, the selected illumination time is displayed on monitor 28 and the practitioner has the option of (1) actuating trigger 22 using the selected time; or (2) adjusting the time then actuating trigger 22. An example of the overriding means includes an integrated circuit electrically coupled to knobs 24, 26, and to the timing means such as the time selecting means.

In one embodiment, system 10 includes a means for selecting between an automatic time selecting mode, an automatic time selecting mode with override capability (or bypass mode), and a manual time selecting mode, such as knob 32 electrically coupled to the time selecting means.

In one embodiment, the automatic time selecting means comprises computing means for computing the illumination time. Examples of the computing means include a computer, a switch, a relay, or a circuit, such as a programmable integrated circuit. Examples of the means for causing the light source means to provide light energy to the photoreactive resin for the selected illumination time include trigger 22 and a switch, computer, circuit, such as a programmable integrated circuit, relay, or other timing mechanism electrically coupled to trigger 22. In one embodiment, the means for causing the light source means to provide light energy for the selected illumination time operates by allowing electricity to flow to the light source means for an illumination time corresponding to the time selected by the time selecting means.

In one embodiment, the time selecting means is integral with the means for causing the light source means to provide light energy to the photoreactive resin. In another embodiment, the time selecting means is separate from the means for causing the light source means to provide light energy to the photoreactive resin.

In either of these embodiments, the timing means may include means for communicating the measurement of the selected illumination time from the time selecting means (such as the manual or automatic time selecting means) to the means for causing the light source means to provide light energy to the photoreactive resin for the selected illumination time. The communicating means may be comprised, for example, of circuitry electrically coupling the time selecting means and the means for causing the light source means to provide light energy to the photoreactive resin for the selected illuminative time.

In one embodiment, the automatic time selecting means selects the illumination time of the partial cure mode based on the metered light intensity and the desired total light energy while the illumination time of the full cure mode is selected by employing the manual time selecting means. In yet another embodiment, the automatic time selecting means selects the illumination times of the both the full cure and partial cure modes based on the metered intensity of the light source means and the desired total light energy. In another embodiment, the automatic time selecting means selects the illumination time of the full cure mode while the partial cure mode illumination time is selected manually.

The time selecting means also includes means for selecting the amount of fine tuning desired, such as knob 34 which selects the smallest increment desired to be displayed on display 28, which is the smallest increment adjusted by the practitioner or the automatic time selecting means. Knob 34 selects the baseline increments such as seconds, tenths of seconds, tens of seconds, and, optionally, hundredths of seconds or other increments for the manual, automatic, or bypass mode. Thus, variable increment capability is available in the automatic, manual, and bypass modes.

Knob 34 thereby selects the amount of fine tuning desired. Thus, if the illumination time is approximately seven seconds and the practitioner only desires to fine tune in the range of seconds, the practitioner may actuate knob 34 to the "seconds" station, then choose the desired seconds using knobs 24, 26. Optionally, the automatic time selecting means chooses the illumination time. If however, the practitioner desires more precision fine tuning into the tenths of seconds, the practitioner actuates knob 34 to the "tenths" of seconds station, as shown in FIG. 1.

In one embodiment, while in the automatic time selecting mode, the automatic time selecting means automatically selects the illumination time required to provide the desired total light energy while knob 34 is used by the practitioner to set the amount of fine tuning desired. For example, if while in the automatic mode the practitioner desires to receive an illumination time precisely measured to the tenth of a second, the practitioner may actuate knob 34 to the tenths station, as shown in FIG. 1.

As discussed below, in one embodiment, the timing means causes the light source means to intermittently provide pulsations of light energy to the photoreactive resin. This may be accomplished, for example, by programming the timing means to, upon actuation of trigger, selectively activate, then deactivate, then reactivate the light source means, such as by alternatively activating, then deactivating, then reactivating the flow of electrical power to the light source means.

IV. Compensating Means

As mentioned above, since the automatic time selecting means compensates for variations in light intensity by increasing the illumination time after decreases in intensity, the automatic time selecting means serves as an example of compensating means for compensating for variations in the intensity of the light source means such that the total light energy provided to the resin is constant despite variations in light intensity.

In one embodiment, the automatic time selecting means increases illumination time in response to decreases in light intensity during actuations. In this embodiment, a sensor of a metering means electrically coupled to the automatic time selecting means senses the light intensity on a constant basis and the automatic time selecting means adjusts for decreases in intensity as they occur.

Thus, a variety of embodiments of compensating means may be programmed with a desired total energy and adjust system 10 to emit the desired total light energy upon receiving a measurement of the intensity of the light source means. These embodiments of the compensating means compensate for a variety of different factors which individually and/or collectively decrease the intensity of the light source means. Examples of such variations include decreases in wattage, decreases in voltage, decreases in amperage, decreases in the quality of the bulb, and other factors causing a decrease in light intensity.

The compensating means can be comprised of a variety of components such as a circuit, switch, monitor, gauge, regulator, relay or a computer which may be programmed with the total light energy output desired by a practitioner and adjusts at least one of the components of the system when the light intensity varies in order to compensate for the variation.

In one embodiment, the compensating means is electrically coupled to the metering means and to the power supply means and responds to a variation in light intensity by varying either the voltage or the current (or both) which is provided to the light source means. In another embodiment, the compensating means is electrically coupled to the metering means and to the power supply means and responds to variations in light energy by increasing or decreasing electrical power to the entire system. In another embodiment, the compensating means is coupled to the metering means and is coupled to or is comprised of the time selecting means.

In another embodiment, the compensating means is separate from the time selecting means, but is electrically coupled to the metering means and to the timing means (such as to the time selecting means) and directs the timing means to increase illumination time. In one embodiment, the compensating means is electrically coupled to at least one of the time selecting means, light source means, power supply means, metering means, and the means for causing the light source means to provide light energy to the photoreactive resin for the selected illumination time.

Also by way of example, in one embodiment, the compensating means, such as the automatic time selecting means, is preprogrammed at the manufacturing stage with a measurement of the desired total light energy. In another embodiment, the practitioner employing the light curing unit inputs the measurement of the desired total light energy prior to actuation. As an example, one embodiment of the compensating means includes calibrating means for calibrating the light curing system with a measurement of the desired total light energy. The calibrating means will be discussed in detail below.

The compensating means may be continually activated or may be selectively activated when desired by the practitioner. In order to provide for selective activation, the compensating means further comprises recalibrating means for selectively recalibrating system 10, an example of which will be discussed in detail below.

System 10 may thus be configured such that the compensating means compensates for variations in light intensity between and/or during actuations. The compensation for intensity variations may occur in the automatic time selecting mode, the bypass mode, and/or the manual time selecting mode. As an alternative to adjusting the illumination time (or in addition thereto), in any of these modes, the compensating means may compensate for variations in intensity, caused by deteriorating bulb condition, for example, by increasing electrical power.

V. Power Supply

The power supply means employed by light cure system 10 is electrically coupled to the light source means, the timing means, and other mechanisms on system 10, such as a compensating means separate from the timing means. Power is, by way of example, in the form of electricity emanating from a wall plug through electrical cord 44. In one embodiment, the 110 AC electricity is transformed to DC current, through the use of a transformer (not shown) in system 10 in order to be compatible with the light source means or other mechanism.

VI. Additional Examples of Use and Manufacture

Figure 2:
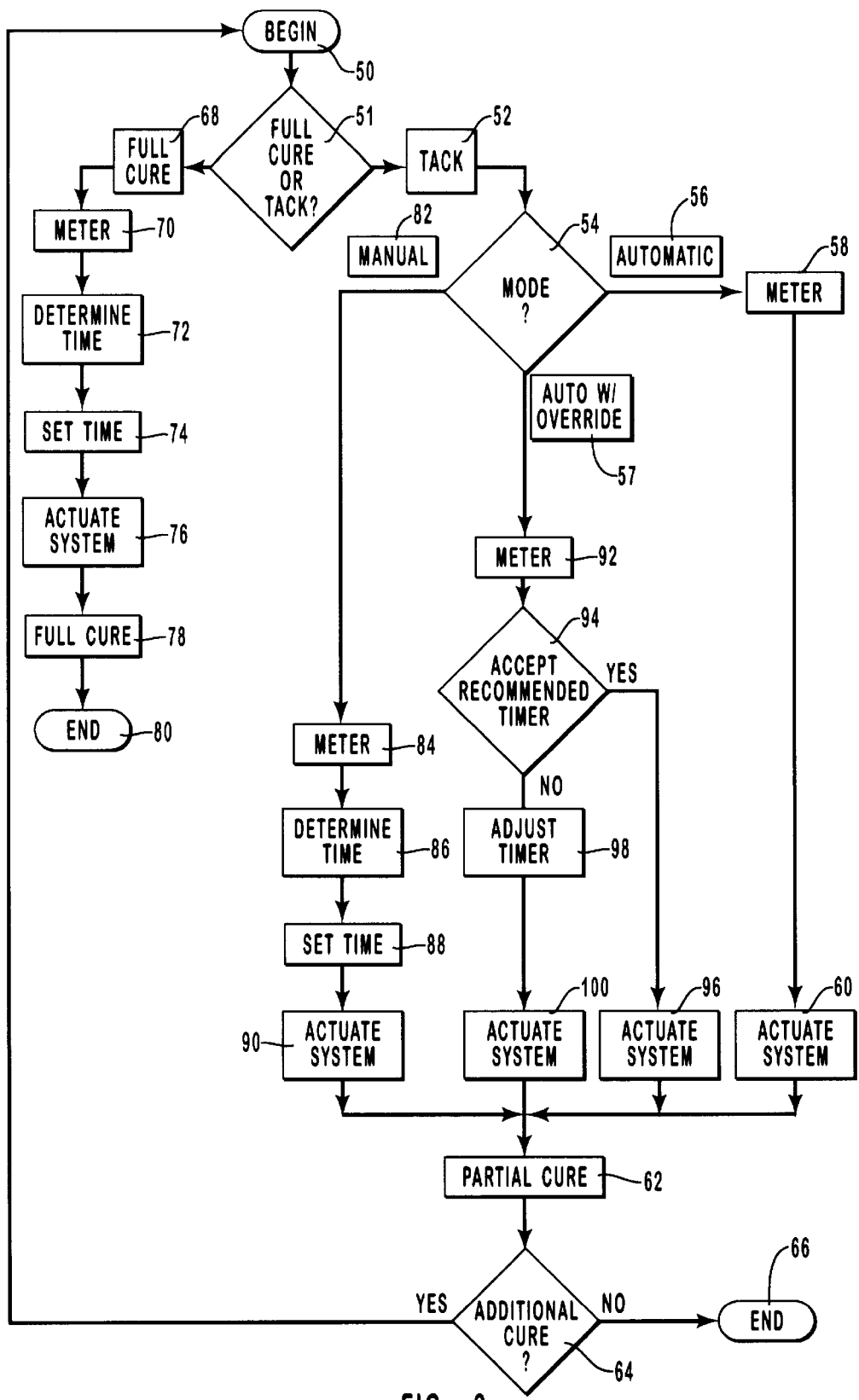
FIG. 2 is a diagram representing certain options and steps available to the practitioner when employing the light curing unit of FIG. 1.

One example of a possible use of system 10 will be provided with reference to the flow chart in FIG. 2. As shown in the flow chart of FIG. 2, in one embodiment, after the beginning step 50, the practitioner confronts decision step 51 decides whether to fully polymerize or tack the photoreactive resin as shown at 51. If tacking is desired, the practitioner selects the tacking mode 52 by actuating knob 21. The practitioner then confronts decision step 54 and decides whether to tack in the automatic time selecting mode 56, in the manual time selecting mode 82, or in the automatic time selecting mode with override capability 57. If the practitioner selects the automatic mode 56, without override capability, the practitioner actuates knob 32 accordingly, then proceeds to meter step 58 and meters the intensity of the light source means. In one embodiment, upon metering the intensity of the light source means, the automatic time selecting means, which is electrically coupled to the metering means, selects an illumination time.

The practitioner then proceeds to actuation step 60 by actuating trigger 22, which results in partial cure 62. At this point, the practitioner may make adjustments such as removing any excess resin or adding additional resin. The practitioner then confronts decision step 64. If additional cure is not desired, the practitioner's use of system 10 is ended at end step 66. If additional cure is desired, the practitioner returns to beginning step 50, and decides whether to tack the photoreactive resin again, or to proceed to full cure step 68 by directing knob 21 to the full cure mode.

It will be appreciated that at this stage, the practitioner is able to meter the intensity of the light source means again.

While it is generally expected that a single actuation will not have a significant effect on the intensity of the light source means, continued use of system 10 generally decreases the intensity of a particular bulb. Nevertheless, in one embodiment, upon measuring the intensity of the light source means, the compensating means compensates for variations in light intensity, such as by increasing illumination time or electrical power.

If full cure is selected, the practitioner then proceeds to meter step 70. In one embodiment, the practitioner then reads display 42, determines the illumination time from a chart or other means, step 72, sets the time, step 74 by adjusting knobs 24, 26, then actuates the system, step 76, resulting in full cure 78. Full cure 78 is thus another end 80 of the process. In another full cure embodiment not shown in FIG. 2, the automatic time selecting means selects the full cure illumination time. In this embodiment, after the practitioner has selected the full cure mode, only metering and actuation are required, similar to steps 58, 60.

If the manual mode 82 is selected at decision step 54, the practitioner meters the light source means in step 84, then manually determines the appropriate time to achieve tacking in step 86, sets the time, step 88, then actuates the system, step 90, resulting in partial cure 62.

If the override option is selected at decision step 54, the practitioner meters the light source means at step 92. Display 28 then displays a recommended time. If the recommended time is accepted at decision step 94, the practitioner then actuates the system at step 96. If the practitioner desires to change the illumination time, the practitioner adjusts the time with knobs 24, 26 at step 98, and actuates the system at step 100, resulting in partial cure 62.

It will be appreciated that in each of the foregoing scenarios, at some point before or during actuation, the practitioner deposits the photoreactive resin in a desired location and positions the light source means adjacent the photoreactive resin. Additional optional steps following actuating the system include, for example: (i) inspecting the photoreactive resin to determine if adjustments such as removal of excess resin or adding additional resin are required; and (ii) making the adjustments by removing the excess resin or adding additional resin.

It will be appreciated that the step of selecting an illumination time may comprise manually selecting the illumination time, such as by using knobs 24. 26, or by employing an automatic selecting means to automatically select the illumination time. Since the light curing system may be actuated for an illumination time having one of the different time increments available, it will also be appreciated that the step of selecting an illumination time may include selecting a time increment from the different time increments available.

In one embodiment, the practitioner is not required to meter the intensity of the light source means before each use. Instead, the time selecting means includes a memory such that the illumination time which was employed in a previous actuation for a particular mode is automatically programmed for the next actuation. For example, in one embodiment, upon activating knob 21 to the tack mode, the illumination time of the previous actuation is programmed and is used upon each new actuation unless the practitioner first meters the intensity of the light source means, resulting in the selection of a new illumination time.

In one embodiment, the light curing system 10 of the present invention is manufactured by electrically coupling a power supply means to a light source means and a timing means. A time selecting means of the timing means, such as an automatic time selecting means, may be electrically coupled to a metering means. The time selecting means selects an illumination time having one or more of the different time increments available on the timing means.

The method of manufacture may include programming the automatic time selecting means to select an illumination time based on a measurement of the desired total light energy and on a measurement of the intensity of the light source means such that the total light energy emitted for achieving the partially-polymerized state is reproducible. In one embodiment, the automatic time selecting means is programmed during manufacture with a measurement of the desired total light energies for the tack mode and for the full cure mode and with an equation relating to the illumination time and the desired total light energy, such as discussed above.

In one embodiment the method of manufacture comprises electrically coupling compensating means for compensating for variations in the intensity of the light source means to at least one of the timing means, light source means, metering means and power supply means, such that the total output of light energy is constant despite variations in intensity. The compensating means may also be programmed with a measurement of the desired total light energy for a particular mode or other desired information.

The compensating means, such as the automatic time selecting means may be programmed such that upon receiving a measurement of a desired total light energy for one or various modes of operation the light curing system produces the desired total energy for the particular mode despite variations in intensity.

VII. Calibrating and Recalibrating The System

In one embodiment, rather than inputting the desired total light energy at the manufacturing stage, an equation relating to the illumination time and the desired total light energy such as discussed above is preprogrammed during the manufacturing stage and the practitioner calibrates the manufactured system with the desired total light energy. First, the practitioner determines the desired total light energy for each of the various modes, then calibrates the light curing system 10 by emitting the desired total light energy for each mode directly into the manufactured light curing system 10, thereby programming system 10 with the desired total light energy. It will be appreciated that "calibration" is one example of a method of programming system 10 with a measurement of the desired total light energy.

For example, in one embodiment, the practitioner calibrates system 10 with a measurement of the desired total light energy for a particular mode by (1) actuating knob 21 to the desired mode; (2) actuating calibrating means for calibrating the light curing system 10 with a measurement of the desired total light energy; then (3) emitting light into sensor 40 or another sensor associated with or integral with system 10 until the desired total light energy for the mode is emitted into system 10.

In one embodiment, the calibrating means includes a calibration button 46 electrically coupled to the compensating means, shown in FIG. 1. By actuating button 46, system 10 is instructed to receive and record a measurement of the desired total light energy. The practitioner actuates calibration button 46, then positions distal end 38 of light source housing 14 adjacent sensor 40 of meter 36 or another sensor, then actuates trigger 22 for an illumination time such that the desired total light energy is emitted into the sensor. A measurement of the desired total light energy is translated from the sensor into the time selecting means or another compensating means, thereby calibrating system 10 with a desired total light energy.

This embodiment requires the practitioner to determine the desired total light energy in advance, and may require the practitioner to meter the initial intensity and determine the initially desired illumination time prior to calibration (e.g., by experimentation on a particular resin to determine the preferred partially-polymerized state or fully polymerized state illumination time for a given intensity). However, by employing this method, the practitioner is able to calibrate system 10 with a measurement of the desired total light energy. Upon being calibrated, system 10 emits the calibrated total light energy upon actuation of system 10.

As discussed above, one embodiment of the calibrating means of system 10 includes recalibrating means for selectively recalibrating system 10. In this embodiment, the practitioner selectively recalibrates the system to adjust for variations in intensity by actuating a recalibrating means for selectively recalibrating system 10. In one embodiment, the recalibrating means includes button 48, which instructs the time selecting means and/or another compensating means to receive a new intensity measurement, but retain the previously programmed total light energy measurement. The practitioner presses button 48, then meters the light source means. The intensity measurement is received by the automatic time selecting means, for example, which selects an illumination time based on the originally programmed total light energy and on the updated intensity measurement, then communicates the updated illumination time to the means for causing the light source means to provide light energy to the photoreactive resin for the selected illumination time.

In another embodiment, rather than increasing the illumination time, the recalibrating means instructs system 10 to increase the voltage, or the amperage provided to the light source means or otherwise adjusts system 10 to reproduce the desired total light energy. The recalibrating means thus compensates for variations in intensity since the original programming. System 10 therefore provides the same total light energy as originally programmed, despite variations in intensity.

In another embodiment, by pressing button 48, the recalibrating means both meters the intensity of the light source means and adjusts for decreases in intensity since the last activation without placing the light source means adjacent sensor 40. This may be accomplished by providing an internal sensor within light source housing 14, as discussed above.

In one embodiment, both the calibrating means and recalibrating means are electrically coupled to the metering means. Both the calibrating means and the recalibrating means may also be electrically coupled to or integral with the timing means such as by being electrically coupled to the automatic selecting means. The calibrating and recalibrating means are electrically coupled to and powered by the power supply means. The calibrating and recalibrating means may be comprised of a variety of components, including a computer, a switch, a regulator, or a circuit.

VIII. Pulsating Mode

In order to more gradually cure the photoreactive resin, and thereby improve the physical properties of the cured resin, light curing system 10 includes a pulsating mode. In the pulsating mode, upon actuating the light curing system, the light source means provides a plurality of pulsations of light energy to the photoreactive resin, each pulsation separated by a respite period. Because of the variable increment capability, the desired time increment for each pulsation may be selected by the practitioner.

In the pulsating mode, the timing means causes the light source means to intermittently provide light energy to the photoreactive resin. Each pulsation has a pulsating time during which the pulsation provides light energy to the photoreactive resin. Thus, in the pulsating mode, the illumination time is the sum of the pulsating times.

As shown in the examples below, in the pulsating mode, the timing means activates the light source means for a first pulsating time, then ceases activation of the light source means for the respite period, then activates the light source means for a second pulsating time, (and so on if desired) thereby providing separate pulsations of light energy. Since the timing means is selectively operable in a plurality of different time increments, the practitioner is able to fine tune the total amount of light energy provided to the photoreactive resin during the pulsating mode.

Figure 3:
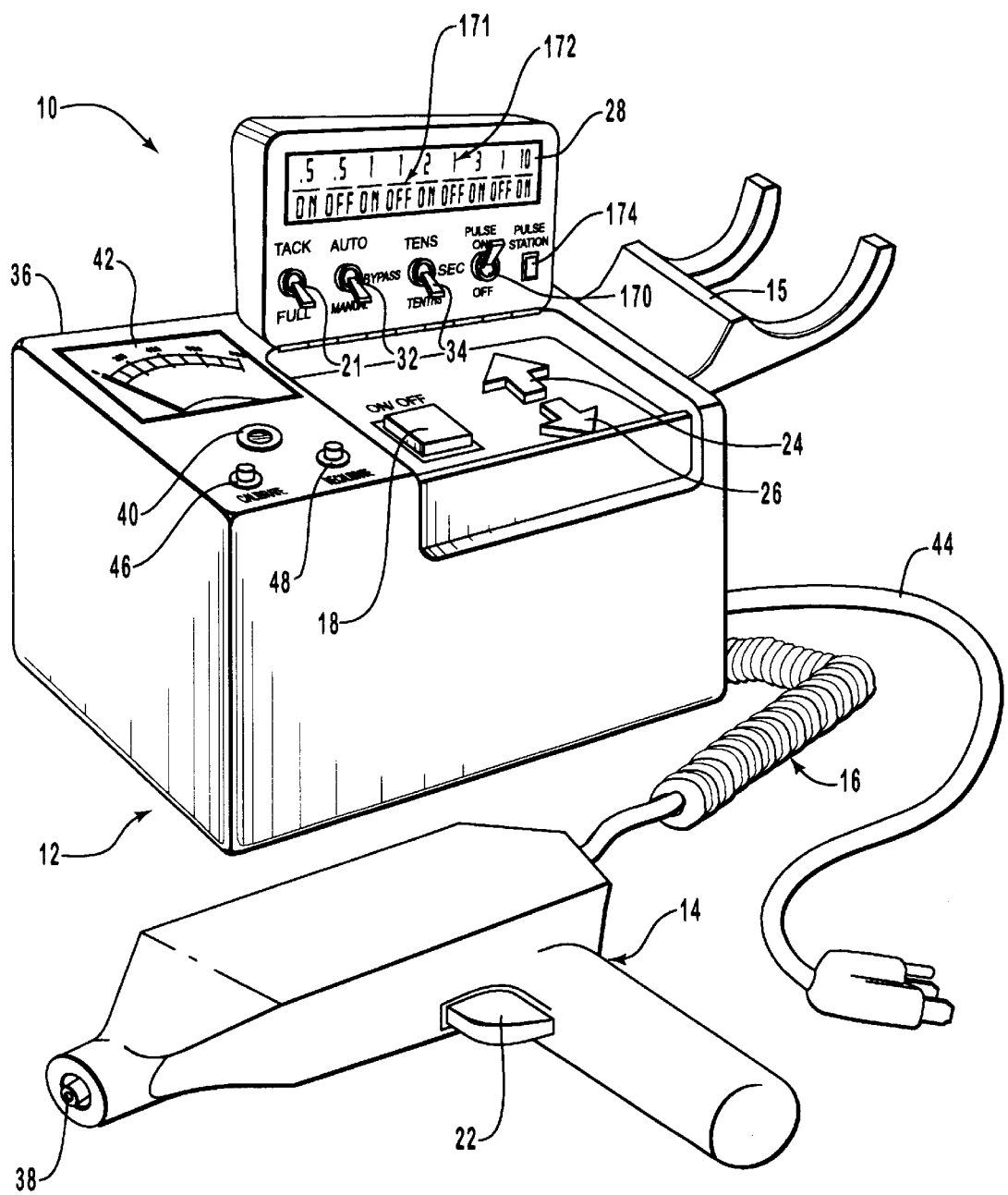
FIG. 3 is a perspective view of the invention of FIG. 1 in a pulsating, manual, full cure mode and having a different illumination time from that in FIG. 1.

In the embodiment of FIG. 1, the pulsating knob 170 is directed to the off position, indicating that the pulsating mode is not selected. By turning the pulsing knob 170 to the on position, however, as shown in FIG. 3, it is possible to provide the desired illumination in a plurality of pulsations in the manual and full cure modes, as shown in FIG. 3, or in the automatic, bypass, and/or tack modes. By providing the illumination in this plurality of pulsations, allowing time between the pulsations in which the system does not illuminate the resin, the overall illumination is more gradual, thereby allowing the resin to form bonds more gradually. It is believed that this strengthens the bonds, reducing shrinkage, stress, and strain on the resin.

As shown in FIG. 3, upon turning pulse knob 170 on, display 28 displays a series of pulse stations 171 which receive the pulsation times and respite period times of a pulse train 172, which includes the desired pulsating and respite times in sequential order. Pulse train stationing knob 174 allows the practitioner to selectively move a cursor to (i) an "on" station, which indicates a pulsating time of one pulsation; or (ii) an "off" station, which indicates a respite period time of a certain respite period. Upon moving the cursor to the desired on or off station, the time for the respective pulsation or respite period may be increased or decreased using knobs 24, 26. If fewer pulsations are desired, the practitioner may place a zero in the desired "on" station or otherwise eliminate a station.

The pulse train may feature a variety of different time sequences, depending on the desired pulsation sequence. While it is desirable to allow the bonds of the resin to form more gradually, this does not necessarily require that each pulsation time gradually increase, although this is one option. Example one demonstrates the pulse train of a plurality of pulsations of light energy separated by a respite period of a selected time. The time for the pulsations and respite period may be selected by the practitioner or by the automatic selecting means.

EXAMPLE 1

| (Time in Seconds) | | |
|---|---|---|
| 1 | 1 | 10 |
| on | off | on |

In one embodiment, the light curing system includes an initial pulsating stage followed by a continuous stage. The continuous stage is a final uninterrupted pulsation. The initial pulsating stage comprises each of the pulsations preceding the continuous stage and each of the respite periods directly following a pulsation preceding the continuous stage. In one embodiment, the initial pulsating stage lasts between about 0.01 to about sixty seconds while the continuous stage lasts for about 0.01 to about sixty seconds or more.

As shown in Example 1, in one pulse train, the initial pulsating stage lasts for two seconds and includes a first pulsation of one second and a respite of one second, while the continuous stage lasts for ten seconds. As shown in FIG. 3 and Example 2, the initial pulsating stage lasts ten seconds and includes a variety of pulsations and respites while the continuous stage lasts for ten seconds. In the pulse train shown in FIG. 3, and in Example 2, the pulsating times also gradually accelerate.

EXAMPLE 2

| (Time in Seconds) | | | | | | | | |
|---|---|---|---|---|---|---|---|---|
| 0.5 | 0.5 | 1 | 1 | 2 | 1 | 3 | 1 | 10 |
| on | off | on | off | on | off | on | off | on |

In another embodiment, as shown in Example 3, the pulsating times gradually accelerate and reach a continuous stage more rapidly than that shown in Example 1.

EXAMPLE 3

| (Time in Seconds) | | | | |
|---|---|---|---|---|
| 1 | 1 | 2 | 1 | 10 |
| on | off | on | off | on |

In another embodiment, as shown in Example 4, the pulsating times begin to accelerate, then level off before reaching a continuous stage.

EXAMPLE 4

| (Time in Seconds) | | | | | | |
|---|---|---|---|---|---|---|
| .2 | .4 | .4 | .4 | .4 | .4 | 10 |
| on | off | on | off | on | off | on |

In another embodiment, as shown in Example 5, the system pulsates without accelerating until reaching the continuous stage.

EXAMPLE 5

| (Time in Seconds) | | | | | | |
|---|---|---|---|---|---|---|
| .5 | .5 | .5 | .5 | .5 | .5 | 10 |
| on | off | on | off | on | off | on |

The total actuation time is the sum of the pulsating times plus the times for each of the respite periods between pulsations. Thus, the light curing system is positioned adjacent the photoreactive resin for the actuation time, during which the system provides pulsations of light energy to the photoreactive resin, each pulsation separated by at least one respite period.

In one embodiment, the initial pulsating stage lasts between about 1 to about 50 seconds, more preferably about 1 to about 30 seconds, during which the light curing system may accelerate, decelerate, or may vary illumination in a number of different combinations thereof. For example, in one embodiment, the initial pulsating stage lasts for about five to about twenty seconds, during which the pulsating times accelerate, followed by the continuous stage. In another embodiment, the initial pulsating stage lasts for about three to about eight seconds, during which the pulsating times accelerate, followed by the continuous stage. In another embodiment, in the initial pulsating stage, the pulsations begin to accelerate, then the system pulsates without accelerating before reaching the continuous stage.

In one embodiment, the pulsations accelerate, then decelerate before reaching the continuous stage. In another embodiment, the pulsations accelerate, then decelerate, then accelerate over a period of about two to about eight seconds before reaching the continuous stage. In yet another embodiment, the pulsations decelerate, then accelerate, then decelerate again before reaching the continuous stage. As shown, these patterns may be varied as desired by the practitioner depending on what is most suitable for the particular resin.

In one embodiment, in the automatic time selecting mode, the automatic time selecting means selects the desired illumination time, which is featured on display 28. The practitioner then actuates pulsating knob 170, after which the practitioner divides the automatically selected illumination time into desired increments. In another embodiment, the automatic time selecting means automatically selects the pulse train desired by the practitioner after the intensity of the bulb is measured and knob 170 is actuated. The pulse mode may be engaged in conjunction with any of the other available modes: automatic, manual, override, tack, full cure, etc. Thus, it is possible to pulsate while tacking, engaging in a full cure, or while using the automatic or manual time selecting modes, for example.

IX. Retrofit

The invention further includes a variety of means for retrofitting system 10 or portions thereof onto existing light curing units which lack the capability of light curing system 10. In one embodiment, system 10 is operable as a stand alone light curing unit, and as a retrofitting device to be retrofit onto other light curing units, thereby providing pulsating capability, variable time increment capability, and/or compensating capability, such as automatic illumination time selection capability to an existing light curing unit.

In another embodiment, a timing means having pulsating capability and/or selectively operable in a plurality of different time increments as discussed with regard to system 10 is retrofit onto an existing light curing unit which is not operable in a variety of different time increments. In another embodiment, an automatic time selecting means is retrofit onto an existing light curing unit lacking an automatic time selecting means. In another embodiment, an automatic time selecting means selectively operable in a plurality of different time increments is retrofit onto an existing light curing unit. A metering means electrically coupled to the automatic time selecting means may also be retrofit along with any of the foregoing embodiments. In another embodiment, another example of a compensating means is retrofit onto an existing unit.

Figure 4:
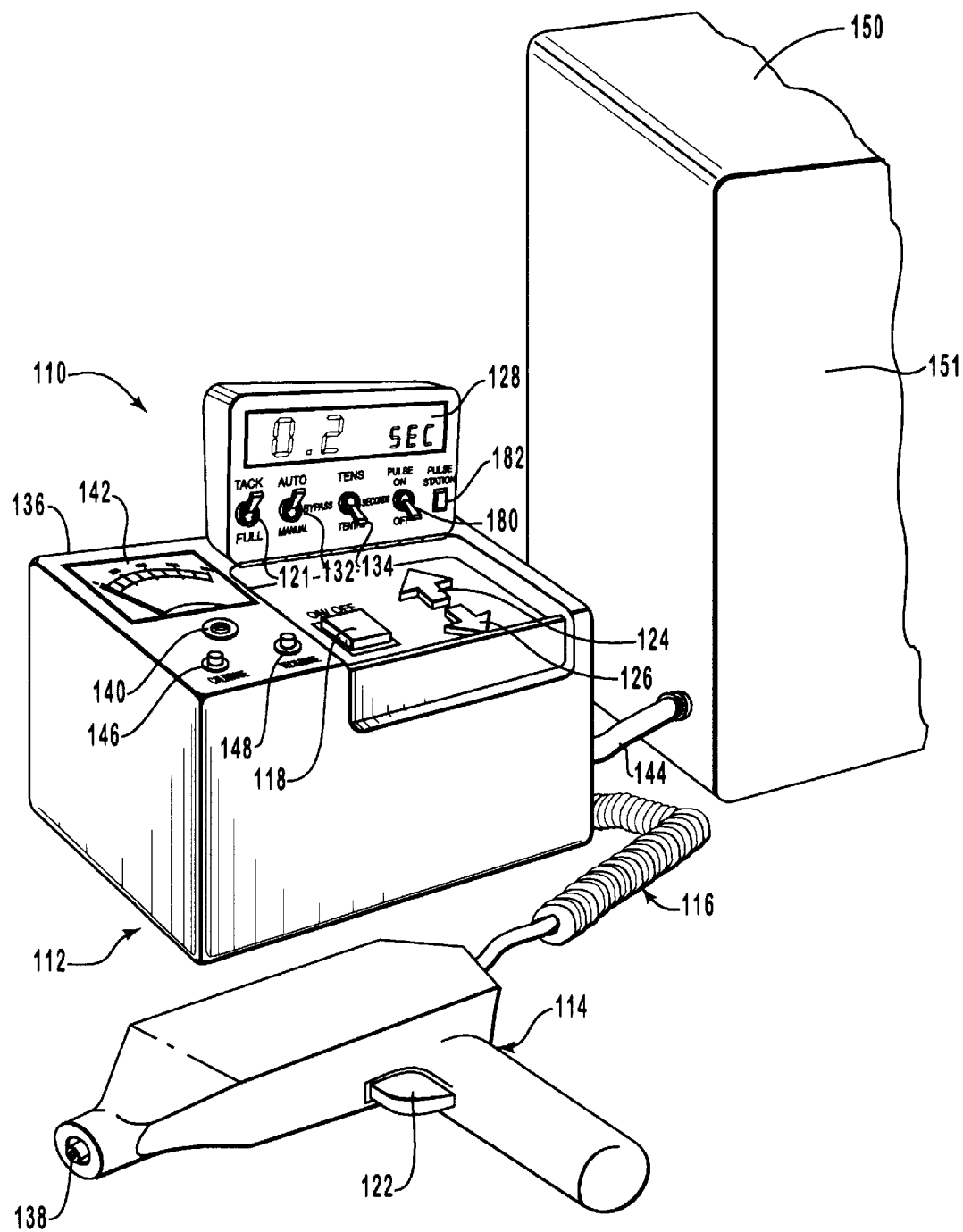
FIG. 4 is a perspective view of a retrofitting device of the present invention.

Also by way of example, as shown in FIG. 4, in one embodiment, retrofit unit 110 provides pulsating capability, variable time increment capability and compensating capability to an existing light curing unit 150. System 110 is capable of being retrofit onto an existing light curing unit 150, causing the existing unit 150 to have any of the benefits and advantages of system 10. In one embodiment, unit 110 is connected between the electrical cord 116 of a light source housing 114 of an existing unit 150 and the main housing 151 of the existing light curing unit 150, causing the existing unit to have the benefits and advantages of system 10. Optionally, unit 110 includes its own light source means and attaches through electrical cord 144 to main housing 151 only.

As discussed above with regard to system 10, in one embodiment, retrofit unit 110 is operable in a full cure mode and a partial cure mode. The partial cure mode is actuated to achieve the partially-polymerized state and the full cure mode is actuated to achieve a fully polymerized state. A compensating means, such as an automatic time selecting means in unit 110 may be programmed to produce a constant reproducible desired total light energy during the partial cure mode and/or full cure mode as discussed above with regard to system 10. The retrofit unit 110 includes a knob 121 for selecting between a tack mode and a full cure mode.

Retrofit unit 110 includes a housing 112 which houses a metering means for measuring the intensity of the light source means, such as meter 136. Meter 136 has a meter display 142 and a sensor 140 for sensing and a meter display 142 for displaying the intensity from distal en 138 of the light source means of light source housing 114. Housing 112 further houses timing means for causing the light source means to provide light energy to the photoreactive resin for an illumination time, during which the light source means provides light energy to the photoreactive resin, the timing means selectively operable in a plurality of different time increments, thereby allowing fine tuning of the total amount of light energy provided to the photoreactive resin. Thus, the photoreactive resin achieves and at least temporarily remains in a partially-polymerized state.

The timing means includes (i) time selecting means and (ii) means for causing the light source means to provide light energy to the photoreactive resin for the selected illumination time. In one embodiment, the time selecting means is an automatic time selecting means such as computing means electrically coupled to the metering means for computing an illumination time. The time selecting means of retrofit unit 110 includes means for selecting the amount of fine tuning desired, such as knob 134, which selects between increments such as minutes, seconds, tenths of seconds, tens of seconds, hundredths of seconds, thousandths of seconds or combinations thereof for a manual, automatic, or bypass mode as discussed above with regard to system 10.

Retrofit unit 110 may include its own power supply means electrically coupled to the components of retrofit unit 110, such as the timing means, a compensating means separate from the time selecting means, or a light source. However, in one embodiment, the retrofit unit 110 is designed to use the power of the existing light curing unit 150 on which the unit 110 is retrofitted. In addition, calibrating and recalibrating means, such as buttons 146, 148 allow the practitioner to calibrate and recalibrate unit 110, as discussed above with regard to system 10.

The retrofit light curing unit 110 optionally includes an "on/off" button 118. The retrofit unit preferably employs an illumination time increase knob 124 and an illumination time decrease knob 126 as discussed above with regard to system 10. Retrofit unit 110 also comprises a knob 132 for selecting between an automatic mode, a fully manual mode, and a bypass mode, as discussed with regard to the system 10. The preferred retrofit unit 110 further includes a display means, such as monitor 128 and an overriding means, as discussed above with regard to system 10.

In one embodiment, the desired total light energy is programmed into retrofit unit 110 such as discussed above with regard to system 10. The equations discussed above with reference to system 10 may also be programmed into retrofit unit 110. The timing means of retrofit unit 110 is electrically coupled to the power supply of the light source means of the existing unit 150 or the timer of the existing unit 150 or both. In another embodiment, the compensating means such as the time selecting means of the retrofit unit 110 is electrically coupled to the power supply of the light source means of the existing unit 150 or the timer of the existing unit 150 or both. Optionally, the timing means of the retrofit unit 110 is electrically coupled to the time selecting means of the existing unit. In the embodiment of FIG. 4, electrical cord 144 extends between unit 110 and unit 150.

The features of retrofit unit 110 may operate on the principle of overriding the time selected on the existing unit 150. By way of example, in one embodiment, after the retrofit unit 110 is coupled to the existing unit 150, the longest possible time duration available on the existing unit 150 is then selected and communicated to the timer of the existing unit 150. The practitioner then meters the light source means. The time selecting means, such as the automatic time selecting means, of the retrofit unit 110 selects an illumination time. Trigger 122 is then actuated. The timing means of the existing unit 150 operates as if it were providing light for the longest possible time duration. However, the retrofit unit 110 overrides the existing unit and the light source means is only actuated for the illumination time selected by the retrofit time selecting means. In one embodiment, unit 110 overrides the existing unit's time selection by terminating the electrical supply of the existing unit's light source means or the electrical power of entire system 150 when the time selected by retrofit unit 110 is reached.

It will also be appreciated that it is also possible for the practitioner to select from a plurality of different time increments on the retrofit unit 110 (as discussed above with regard to system 10), which overrides the time increment selected by the existing unit 150, in a manual, automatic, or bypass mode, such as by selecting the largest increment or time duration possible on the existing unit 150, then terminating the electrical supply of the existing unit's light source means when the desired increment is achieved.

In one embodiment, rather than fitting between the light source housing and the main housing 151, as shown in FIG. 4, retrofit unit 110 is coupled between the power cord (not shown) of main housing 151 and the electrical source of main housing 151, such as an electrical outlet. For example, unit 110 may be plugged into the outlet, while existing unit 150 is coupled to unit 110, unit 110 thereby providing power to the existing unit 150, and regulating existing unit 150 by regulating the power supply of existing unit 150. In this embodiment, the light source housing of the existing unit 151 remains coupled to the existing unit 151 and is employed to cure the resin. Also in this embodiment, and in any of the foregoing embodiments, retrofit unit 110 may include its own transformer.

In yet another embodiment, the retrofit unit 110 contains all or nearly all of the components of system 10. For example, retrofit unit may contain each of the components of system 10, with the exception of the transformer, the "on" and "off" switch, the power cord 44, the electrical cord 16, and the light source housing 14. In this embodiment, system 110 employs the light source housing and light source means of the existing unit.

Retrofit unit 110 also has a pulsating mode selectively actuated through the use of pulsating knob 180, causing a unit 150 which does not otherwise pulsate to pulsate. Unit 110 also features pulse train station knob 182 which functions as the equivalent of pulse train station 174 on unit 10. Unit 182 allows practitioner to set the pulsating time and the respite time of one pulsation in a variety of time sequences.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A light curing system for polymerizing photoreactive resin, comprising:
   light source means for providing light energy to the photoreactive resin, the light source means having an intensity;
   timing means for causing the light source means to provide light energy to the photoreactive resin for an illumination time, during which the light source means provides light energy to the photoreactive resin, the timing means selectively operable in a plurality of different time increments so as to more finely tune total time exposure of the photoreactive resin, including a first time increment and a second time increment that is different in duration from the first time increment, such that the illumination time is a sum of an integer multiple of the first time increment and an integer multiple of the second time increment; and
   power supply means electrically coupled to the light source means and the timing means for supplying electrical power to the light source means and the timing means.

2. A light curing system as in claim 1, wherein the timing means comprises time selecting means for selecting the illumination time.

3. A light curing system as in claim 2, further comprising:
   metering means for measuring the intensity of the light source means, wherein the time selecting means comprises automatic time selecting means electrically coupled to the metering means for automatically selecting the illumination time.

4. A light curing system as in claim 3, further comprising overriding means for manually overriding the illumination time selected by the automatic time selecting means.

5. A light curing system as in claim 3, wherein
   the light curing system is operable in a partial-cure mode, the partial-cure mode actuated to partially polymerize the resin, and
   the automatic time selecting means is programmed with a value of a predetermined total light energy for partially polymerizing the resin, such that the light curing system produces a substantially reproducible total light energy while operating in the partial-cure mode.

6. A light curing system as in claim 1, wherein the light curing system comprises a pulsating light curing system, the light source means providing a plurality of pulses of light energy to the photoreactive resin.

7. A light curing system as in claim 1, further comprising compensating means for compensating for variations in the intensity of the light source means.

8. A light curing system as in claim 7, further comprising recalibrating means for selectively recalibrating the total energy produced by the system to adjust for variations in the intensity.

9. A light curing system as in claim 1, wherein the time increment of the illumination time is selected from the group of increments consisting of thousandths of a second, hundredths of a second, tenths of a second, seconds, tens of seconds, minutes, and combinations thereof, such that the total amount of light energy is substantially reproducible to achieve a predetermined amount of polymerization.

10. A light curing system as in claim 1, wherein the timing means is retrofit onto an existing light curing system.

11. A light curing system for polymerizing photoreactive resin, comprising:
    light source means for providing light energy to the photoreactive resin, the light source means having an intensity;
    timing means for causing the light source means to provide light energy to the photoreactive resin for an illumination time, during which the light source means provides light energy to the photoreactive resin;
    automatic time selecting means for automatically selecting the total illumination time based on a value of a predetermined total light energy to be emitted by the light source, and on a measurement of the intensity of the light source means; and
    power supply means electrically coupled to the light source means and the timing means, for supplying electrical power to the light source means, the compensating means, and the timing means.

12. A light curing system as in claim 11, wherein the timing means includes time selecting means for selecting the illumination time.

13. A light curing system as in claim 12, further comprising metering means electrically coupled to the automatic time selecting means for measuring the intensity of the light source means.

14. A light curing system as in claim 11, wherein the timing means is selectively operable in a plurality of different time increments.

15. A light curing system as in claim 11, further comprising calibrating means for initially calibrating the light curing system in response to a measurement of a predetermined total light energy made at the light curing system.

16. A light curing system as in claim 15, further comprising recalibrating means for selectively recalibrating the total energy produced by the system to adjust for variations in the intensity.

17. A light curing system for polymerizing photoreactie resin, comprising:
    light source means for providing light energy to the photoreactive resin, the light source means having an intensity;
    metering means for measuring the intensity of the light source means;
    timing means for causing the light source means to provide light energy to the photoreactive resin for an illumination time, during which the light source means provides light energy to the photoreactive resin, the timing means including automatic time selecting means electrically coupled to the metering means for automatically selecting the illumination time based on a value of a predetermined total light energy to be emitted by the light source, and on a measurement of the intensity of the light source means; and power supply means electrically coupled to the light source means and the timing means for supplying electrical power to the light source means and the timing means.

18. A light curing system as in claim 17, further comprising calibrating means for initially calibrating the light curing system in response to a measurement of a predetermined total light energy made at the light curing system.

19. A light curing system as in claim 17, wherein
the light curing system is operable in a partial-cure mode, the partial-cure mode actuated to partially polymerize the resin, and
the automatic time selecting means includes data representing a value of a predetermined total light energy for partially polymerizing the resin, such that the light curing system produces a reproducible predetermined total light energy while operating in the partial-cure mode.

20. A light curing system as in claim 17, wherein the automatic time selecting means automatically selects the illumination time based on a value of a predetermined total light energy and on a measurement of the intensity of the light source means.

21. A light curing system as in claim 17, wherein the timing means is selectively operable in a plurality of different time increments.

22. A light curing system for polymerizing photoreactive resin, the light curing system including
(a) light source means for providing light energy to the photoreactive resin, the light source means having an intensity;
(b) timing means for causing the light source means to provide light energy to the photoreactive resin for an illumination time, during which the light source means provides light energy to the photoreactive resin; and
(c) power supply means electrically coupled to the light source means and the timing means for supplying electrical power to the light source means and the timing means, wherein the improvement comprises:
metering means for measuring the intensity of the light source means, and wherein the timing means comprises automatic time selecting means electrically coupled to the metering means for automatically selecting the illumination time based on a value of a predetermined total light energy to be emitted by the light source, and on a measurement of the intensity of the light source means, the automatic time selecting means programmed such that the light curing system produces a substantially reproducible total light energy.

23. A light curing system as in claim 22, wherein the improvement further comprises the timing means being selectively operable in a plurality of different time increments, such that the photoreactive resin achieves and remains in a partially-polymerized state for at least some measurable period.

24. A pulsating light curing system for polymerizing photoreactive resin, comprising:
light source means for providing light energy to the photoreactive resin, the light source means having an intensity;
timing means for causing the light source means to provide light energy to the photoreactive resin for a predetermined total light energy, including a plurality of pulses that are selectively variable in duration from one another; and
power supply means electrically coupled to the light source means and the timing means for supplying electrical power to the light source means and the timing means and for providing a plurality of pulses of light energy to the photoreactive resin during the illumination time.

25. A light curing system as in claim 24, wherein each pulse has a duration during which light energy is provided to the photoreactive resin, the illumination time being the sum of the durations of the pulses.

26. A light curing system as in claim 24, wherein each pulse is separated from another pulse by a respite period.

27. A light curing system as in claim 24, wherein the light curing system includes an initial pulsating period followed by a continuous stage wherein the system provides continuous light energy devoid of pulses.

28. A light curing system as in claim 24, wherein the timing means causes the light source means to intermittently provide the pulses each pulse being separated from another pulse by a respite period.

29. A light curing system as in claim 24, wherein the timing means is selectively operable in a plurality of different time increments.

30. A method for manufacturing a light curing system for polymerizing photoreactive resin, the method comprising electrically coupling power supply means for supplying electrical power to:
(i) light source means for providing light energy to the photoreactive resin, the light source means having an intensity; and
(ii) timing means for causing the light source means to provide light energy to the photoreactive resin for an illumination time, during which the light source means provides light energy to the photoreactive resin, the timing means selectively operable in a plurality of different time increments so as to more finely tune total time exposure of the photoreactive resin, including a first time increment and a second time increment that is different in duration from the first time increment, such that the illumination time is a sum of an integer multiple of the first time increment and an integer multiple of the second time increment.

31. A method for manufacturing a light curing system for polymerizing photoreactive resin, the method comprising:
electrically coupling power supply means for supplying electrical power to:
light source means for providing light energy to the photoreactive resin, the light source means having an intensity; and
timing means for causing the light source means to provide light energy to the photoreactive resin for an illumination time, during which the light source means provides light energy to the photoreactive resin, the timing means including automatic time selecting means for automatically selecting the illumination time based on a value of pre-determined total light energy to be emitted by the light source and on a measurement of light intensity from the light source means; and
electrically coupling the automatic time selecting means to metering means for measuring the intensity of the light source means.

32. A method as in claim 31, further comprising programming the automatic time selecting means to select the illumination time based on a value of a predetermined total light energy and on a measurement of the intensity of the light source means.

* * * * *

UNITED STATES PATENT AND TRADEMARK OFFICE
CERTIFICATE OF CORRECTION

PATENT NO. : 6,103,203
DATED : August 15, 2000
INVENTOR(S) : Dan E. Fischer

It is certified that error appears in the above-identified patent and that said Letters Patent is hereby corrected as shown below:

Col. 3, ln. 12: after "timer" and before "selectively" delete [is]

Col. 12, ln. 35: after "of" and before "both" delete [the]

Col. 21, ln. 25: after "mode." insert -- Housing 114 had a distal end 138.--

Col. 21, ln. 30: after "intensity" insert --of the light source means--

Col. 21, ln. 30: after "distal" change "en" to --end--

Col. 21, lns. 30-31: after "of" delete [the light source means of]

Col. 22, ln. 40: before "150" change "system" to --unit--

Signed and Sealed this

Twenty-ninth Day of May, 2001

*Attest:*

NICHOLAS P. GODICI

*Attesting Officer*     *Acting Director of the United States Patent and Trademark Office*